United States Patent [19]

Choate

[11] Patent Number: 5,137,151
[45] Date of Patent: Aug. 11, 1992

[54] INSTRUMENT RACK

[76] Inventor: Carol A. Choate, 1062 Manderly Dr., Milford, Mich. 48042

[21] Appl. No.: 799,705

[22] Filed: Nov. 26, 1991

Related U.S. Application Data

[63] Continuation of Ser. No. 568,411, Aug. 16, 1990.

[51] Int. Cl.$^5$ .............................................. B65D 85/00
[52] U.S. Cl. ...................................... 206/370; 206/438; 211/120
[58] Field of Search ............... 211/70.6, 120; 206/370, 206/363, 438

[56] References Cited

U.S. PATENT DOCUMENTS

| | | | |
|---|---|---|---|
| 1,240,706 | 9/1917 | Gropengieser | 211/120 X |
| 2,559,636 | 7/1951 | King et al. | 206/370 |
| 3,094,129 | 6/1963 | Wills | 211/120 X |
| 3,925,014 | 12/1975 | Langdon | 211/13 X |
| 4,135,868 | 1/1979 | Schainholz | 211/60.1 X |
| 4,223,791 | 9/1980 | Taggart | 211/120 |
| 4,229,420 | 10/1980 | Smith et al. | 206/363 X |
| 4,342,391 | 8/1982 | Schainholz | 211/70.6 X |
| 4,577,755 | 3/1986 | Ramsay | 206/370 |
| 4,643,303 | 2/1987 | Arp et al. | 206/370 |
| 4,865,821 | 9/1989 | Langdon | 206/370 X |
| 5,046,624 | 9/1991 | Murphy et al. | 211/70.6 |

*Primary Examiner*—Paul T. Sewell
*Assistant Examiner*—Jacob K. Ackun, Jr.
*Attorney, Agent, or Firm*—Reising, Ethington, Barnard, Perry & Milton

[57] ABSTRACT

An instrument rack (10) for supporting a plurality of instruments (12) includes a wound wire for positively gripping a plurality of instruments (12) between the loops (50) thereof and a support structure operatively connected to the wound wire (28) for maintaining the instruments (12) gripped by the wound wire (28) spaced from a support surface (32).

6 Claims, 1 Drawing Sheet 5,137,151

INSTRUMENT RACK

This application is a continuation of application Ser. No. 568,411, filed Aug. 16, 1990.

TECHNICAL FIELD

The present invention relates to the handling of instruments and particularly surgical instruments which must be sterilized and carried securely into an operating room. More specifically, the present invention relates to an instrument rack or carrying device for surgical instruments which retains the instruments in a selected position.

BACKGROUND OF THE INVENTION AND SUMMARY

Present day surgical procedures regularly use sets of pre-selected surgical instruments for a specified surgical procedure. These instruments are regularly grouped together to form a set. The set is sterilized and stored on a tray or pan and eventually transported on the tray to an operating area for use as required. Examples of such racks are disclosed in U.S. Pat. Nos. 3,925,014 to Langdon, issued Dec. 9, 1975, 4,135,868 to Schainholz, issued Jan. 23, 1979, 4,294,290 to Smith et al, issued Oct. 21, 1980, 4,342,391 to Schainholz, issued Aug. 3, 1982, 4,577,755 to Ramsay, issued Mar. 25, 1986, and 4,641,749 to Link et al, issued Feb. 10, 1987.

Many of the above-mentioned prior art patents provide means for supporting the instruments in an upright position and maintaining scissor-like instruments in a open condition to allow for sterilization of portions of the instruments which would not be exposed to sterilization if the instruments were in the closed condition. For example, the Langon patent discloses a rack comprising an open frame and a pair of removable retaining bars which selectively hold the instrument in an open condition during sterilization to retain the instruments on the rack until use thereof is desired. Instruments such as scissor-like instruments which include lock boxes for locking the instruments in a closed position must be held open to expose portions of the lock boxes as well as any over-lapping scissor portions. A problem exists with this type of rack because a single rod is used to maintain the instruments in an open condition. To have access to any of the instruments, the rod retaining the instruments in the open condition must be removed from all of the instruments or at least a portion of the instruments. The rod further helps to maintain the instruments in an upright position. Once the rod is removed to have access to the remainder of the instruments, the instruments can be tilted and fall together thereby removing the alignment and spacing of the instruments on the rack, as well as contaminating the once sterile instruments.

Several other of the above discussed patents include various other means for maintaining the instruments in an upright position and in an open condition. For example, the Smith et al patent discloses a surgical instrument rack which includes a plurality of upstanding spaced portions for seating instruments therein and maintaining the instruments in an upright position. The rack further includes a second portion which is connectable to the first portion for maintaining the instruments in an open condition. Again, similar to the prior art patents discussed above, removal of the second rack portion to provide access to one instrument allows all of the remaining instruments to be able to close and possibly fall off of the rack.

The present invention addresses the problems set forth above by providing means for positively gripping the instruments held on the subject instrument rack thereby maintaining the instruments in an upright position. If the instruments are the type of instrument which can be opened, such as a scissor-like instrument, the present invention further can maintain the instruments in an open condition whether or not a secondary member, such as a rod, is used to hold the instruments in an open condition.

SUMMARY OF THE INVENTION

In accordance with the present invention, there is provided an instrument rack for supporting a plurality of instruments, the rack including gripping means for positively gripping a plurality of instruments held in the rack and support means operatively connected to the gripping means for maintaining the instruments gripped by the gripping means spaced from a support surface.

FIGURES IN THE DRAWINGS

Other advantages of the present invention will be readily appreciated as the same becomes better understood by reference to the following detailed description when considered in connection with the accompanying drawings wherein.

DETAILED DESCRIPTION OF THE INVENTION

Figure 1:
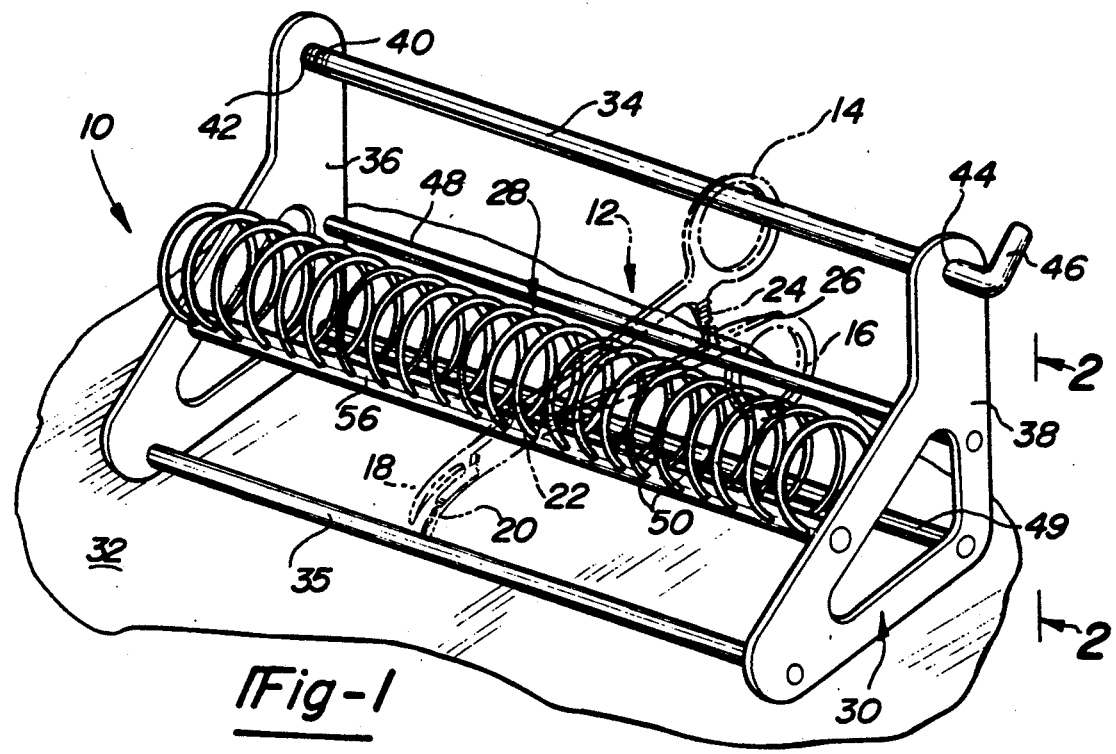
FIG. 1 is a perspective view of a rack made in accordance with the present invention.
Figure 2:
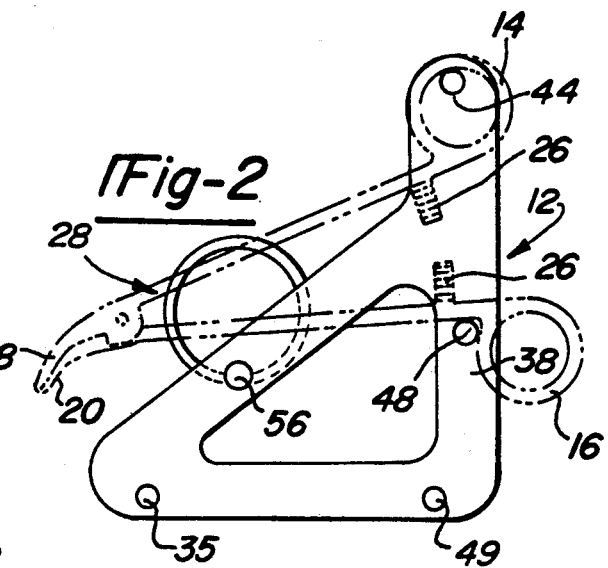
FIG. 2 is a side view of the subject invention taken substantially along lines 2—2 of FIG. 1.
Figure 3:
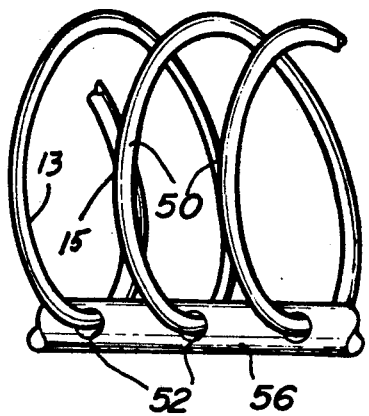
FIG. 3 is an enlarged fragmenting view of the spirally wound wire through the support rod thereof.

An instrument rack for supporting a plurality of instruments constructed in accordance with the present invention is generally shown at 10 in the drawings. Although the rack is shown in FIG. 1 supporting a scissor-like instrument 12 having a pair of handles 14 and 16, two gripping end portions 18, 20, a pivot point 22 therebetween and a pair of lock boxes 24, 26, the instrument rack mode in accordance with the present invention could be used for other instruments which are not scissor-like, such as scalpels and the like. Generally, the instrument rack 10 is characterized by including gripping means generally indicated at 28 for positively gripping a plurality of instruments 12 and support means generally indicated at 30 operatively connected to gripping means 28 for maintaining the instruments 12 gripped by the gripping means 28 spaced from a support surface 32.

The gripping means includes pairs of abutting surface portions, each pair including to surfaces 13,15 facing each other, for abutting against an instrument inserted there between and maintaining the instrument 12 in a open condition when the instruments are inserted therein in an open condition, as shown in FIG. 1. That is, unlike prior art racks, which may include a solid member abutting between the handles of an instrument to maintain the instrument upright and open until the abutting portions are removed, such that all of the instruments close or the instruments are in racks where a rod extends through one of the handles of all of the instruments such that removal of the rod allows for the instruments to fall on each other as well as allowing for closure of all of the instruments, the present invention provides means in the form of gripping means which positively grip the instrument supported by the rack and thereby maintain the instrument in an upright and open condition when the instrument is inserted into the gripping means in an upright and open condition. Thus, the instrument is maintained in an upright and open condition during a sterilization procedure and further is maintained in an upright and open condition until the instrument is either closed manually or is removed from the rack. Removal of other instruments does not result in the disturbance or closure of all other instruments in the rack.

More specifically, the support means 30 includes handle support means in the form of a rod member 34 operatively connected to and spaced from the gripping means 28 for supporting at least one of the handles 14 of the instruments 12 as an intermediate portion of the instrument 12 is gripped by the gripping means 28. The gripping means maintains the instrument in an upright spaced and open condition.

The support means 30 further includes spaced support portions 36, 38 in the form of end plates 36, 38. The rod 34 extends between and is supported by the end plates 36, 38. More specifically, the rod 34 has a first end portion 40 which is threaded within a threaded bore 42 in end plate 36. End plate 38 includes a larger opening 44 extending therethrough, the rod member 34 freely extending through the opening 44 in sliding engagement therewith. The rod member 34 further includes a handle portion 46 which can be gripped by the operator for threading the end portion 40 into the opening 42 or unthreading the end portion 40 from the opening 42.

A second rod member 48 extends between the end plates 36 and 38 and is spaced from and positioned below the rod member 34. The arm supporting handle 16 of the instrument would rest on the rod 48 while the rod 34 extends through handle 14 of the instrument 12. Rods 35, 48 further contribute to supporting the instrument 12 in an upright and open condition, even though removal of rod 34 from handle 14 would not result in the dislodging or closing of the instrument 12 as the gripping means 28 would positively grip the instrument 12 thereby maintaining it in an upright and open condition. However, the rod 34 prevents any accidental closure of the instrument 12 due to any physical force acting upon the rack, such as the rack falling or being manually contacted.

Another rod member 48 extends between end plates 36 and 38 and provides gripping means support means operatively connected to each of the end support plates 36, 38 and extending therebetween. The gripping means 28 comprises a wound wire 28 supported by the rod 56. The wound flexible wire defines biasing means extending from the rod 56 which are operatively connected to the end support plates 36, 38 extending therebewteen. The biasing means including the aforementioned abutting portions. These biasing means in the form of the extending loops 50 of the wound wire are deflectable for allowing insertion of the instruments 12 therebetween and for biasing against the inserted instruments 12 for positively gripping the inserted instruments 12. That is, the wound wire 28 includes a series of the continuous loops 50, each of the loops 50 defining one of the biasing means.

The rod 56 includes a plurality of openings 52 extending over the length of the rod 56, the wound wire 28 being threaded through each of the openings 52 such that the openings 52 provide spacing means for spacing at least a portion of each of the loops 50 from the adjacent ones of the loops 50 even when the remainder of the loop 50 is biased towards an adjacent one of the loops 50 as the result of the insertion of an instrument 12. In other words, each of the openings 52 engages a portion of each of the loops 50 of the wound wire 28 thereby maintaining those portions of the wound wire 28 in a spaced condition even when the remainder of the loop 50 is biased due to the insertion of an instrument 12.

The rack 10 may include further rod members 54, 56 for further securing the rack assembly together.

In operation, the instrument is inserted in between two of the loops 50 such that the loops abut against and grip the instrument 12 in an upright and open condition. Once a set of instruments or a single instrument, depending upon the desired amount of instruments to be used, are inserted into the gripping means 28, and if they are of the type of instruments having an open and closed condition, the instruments are opened or inserted in an open condition. In the open condition, the rod 34 is inserted through the handles 14 of each of the instruments thereby securely maintaining the instruments in an open condition. Upon use of the instrument, the rod 34 is unthreaded from the opening 42 and removed from the rack. The gripping means 28 maintains each of the instruments in an upright and open condition until they are used. Alternatively, and if desired, each of the instruments can be moved into a closed position yet still gripped by the gripping means 28 and maintained on the rack. Thusly, the possibility of the instruments either falling off of the rack or accidently closing are minimized.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims wherein reference numerals are merely for convenience and are not to be in any way limiting, the invention may be practiced otherwise than as specifically described.

What is claimed is:

1. An instrument rack (10) for supporting a plurality of instruments (12), said rack (10) comprising: gripping means (28) including a plurality of pairs of spring-like abutting surface portions (13, 15) for positively gripping and separating a plurality of instruments (12) independently and individually between each of said abutting surface portions (13, 15) and support means (30) operatively connected to said gripping means (28) for maintaining each of the instruments (12) individually and independently gripped by said gripping means (28) and spaced from each other and a support surface (32), said support means including handle support means spaced from said spring-like abutting surface portions (13,15) for supporting at least one of the handles (14) of the instruments (12) independent of said spring-like abutting surface portions (13,15) as an intermediate portion of the instrument (12) is gripped by said spring-like abutting surface portions (13,15), said spring-like abutting surface portions (13,15) maintaining the instruments in an upright spaced and open condition independent of said handle support means allowing independent insertion and removal of the instruments between pairs of said abutting surface portions (13, 15) while other instruments remain spaced and upright between others of said spring-like abutting surface portions (13,15).

2. An instrument rack (10) as set forth in claim 1 wherein said support means includes spaced end support portions (36, 38), said handle support means (34) extending therebetween and being supported thereby, said gripping means (28) including a plurality of upwardly extending and spaced biasing means operatively connected to said end support portions (36, 38) and extending therebetween and including said abutting surface portions, said biasing means being deflectable for allowing the insertion of an instrument (12) therebetween and for biasing against the inserted instrument (12) for positively gripping the inserted instrument (12).

3. An instrument rack (10) as set forth in claim 2 wherein said support means further includes gripping means support means (41) operatively connected to each of said end support portions (36, 38) and extending therebetween, said biasing means including a wound wire member (28) operatively connected to said gripping mean support means (56), said wire comprising a series of continuous loops (50), each of said loops (50) defining one of said biasing means.

4. An instrument rack (10) as set forth in claim 3 wherein said gripping means support means including spacer means for spacing at least a portion of each of said loops (50) from the adjacent one of said loops (50) even when the remainder of said loop (50) is biased towards an adjacent one of said loops (50) as the result of the insertion of an instrument (12).

5. An instrument rack (10) as set forth in claim 4 wherein said spacing means including a plurality of spaced openings (52) extending over a length of said gripping means support means (56), said wound wire (28) being threaded through each of said openings (52), each of said openings (52) engaging a portion of each of said loops (50) of said wound wire (28).

6. An instrument rack (10) as set forth in claim 1 wherein said handle support means includes a rod member (34) extending through one of said end support portions and being removably connected to the other of said end support portions.

* * * * *